United States Patent [19]
Koczab et al.

[11] Patent Number: 5,908,412
[45] Date of Patent: Jun. 1, 1999

[54] COATED NON-WOVEN MATERIAL, ITS MAKING PROCESS AND ITS USE IN A DISPOSABLE ABSORBENT HYGIENE ARTICLE

[75] Inventors: Jean Pierre Koczab, Bondues; Michel Degrand, Bernay; Jean Demessance, Champs-sur-Marne, all of France

[73] Assignees: Peaudouce, Linselles; Elf Atochem, Puteaux, both of France; Corovin GmbH, Peine, Germany

[21] Appl. No.: 08/682,694
[22] PCT Filed: Feb. 8, 1995
[86] PCT No.: PCT/FR95/00149
  § 371 Date: Oct. 3, 1996
  § 102(e) Date: Oct. 3, 1996
[87] PCT Pub. No.: WO95/21957
  PCT Pub. Date: Aug. 17, 1995

[30] Foreign Application Priority Data

Feb. 9, 1994 [FR] France .................................. 94 01659

[51] Int. Cl.$^6$ .............................. A61F 13/15; A61F 13/20
[52] U.S. Cl. .......................... 604/367; 604/366; 604/370; 428/319.7
[58] Field of Search ..................................... 604/366–377; 428/319.7

Primary Examiner—John G. Weiss
Assistant Examiner—Ki Yong O
Attorney, Agent, or Firm—Burns, Doane, Swecker & Mathis, L.L.P.

[57] ABSTRACT

A coated non-woven material, method of making such material, and disposable absorbent hygiene article are disclosed. The coated non-woven material comprises a base layer made of a non-woven web of fibrous material and at least one layer of a thermoplastic film. The peel strength of the material is equal to or below $98 \times 10^{-3}$ kN/m, as measured according to the NFT 76-112 standard, wherein the peeling angle is specified at 180° and the pull speed is specified at 200 mm/mn. In one embodiment, the coated non-woven material is incorporated into a disposable diaper as a liquid-impervious backsheet.

22 Claims, 2 Drawing Sheets

COATED NON-WOVEN MATERIAL, ITS MAKING PROCESS AND ITS USE IN A DISPOSABLE ABSORBENT HYGIENE ARTICLE

BACKGROUND OF THE INVENTION

The present invention concerns a coated non-woven material comprising a base layer made of a fibrous non-woven web and at least one layer made of a thermoplastic film which has been applied under heat onto one face of the base layer. The coated non-woven material can be used, in particular, in disposable absorbent hygiene articles such as diapers for babies or incontinent persons as well as training pants and sanitary napkins comprising a liquid impervious backsheet, a liquid permeable topsheet and an absorbent pad disposed between the backsheet and the topsheet and bonded at least to the internal face of the backsheet, for making, in particular, the backsheet which usually is made of a thin polyethylene film, to impart to this backsheet with a fabric-like or textile appearance and tactile impression, more agreeable for the user.

The invention also concerns a process for making such a coated non-woven material.

It is known in the art to coat fibrous non-woven materials with a thermoplastic film. Such a material is disclosed in patent GB 1 403 603. However, this patent does not give any indication about adhesivity between the two layers, or the textile appearance of the resulting product.

EP 0 187 725 discloses a coated fabric comprising a base layer made of a fibrous non-woven material in which densified and non-densified portions are preformed and a thermoplastic film hot bonded onto one face of said base layer so that the penetration depth of the film within the base layer is limited to less than the total thickness of the basic layer.

According to this patent, such a penetration depth of the thermoplastic film within the base layer is necessary to obtain an improved adhesion of the thermoplastic film to the fibrous non-woven material of the base layer.

However, penetration of the thermoplastic film (which may range from 10 to 250 micrometers) within the fibrous non-woven material, which is enhanced by temperature and pressure during the manufacturing process, becomes a major drawback since a significant amount of the melted thermoplastic film may penetrate into non-densified areas of the fibrous non-woven material, resulting in a decrease in the fabric-like tactile, impression and softness of the uncoated face of the fibrous material.

SUMMARY OF THE INVENTION

A coated non-woven material having improved softness and fabric-layer tactile impression has been discovered, which comprises a base layer made of a fibrous non-woven web and at least one layer of a thermoplastic film, and which is characterized in that the thermoplastic film applied onto the base layer made of a fibrous non-woven web has a peel strength, as determined according to NFT 76-112 standard (peeling angle:180°; pulling speed:200 mm/mn) which is equal to or less than $98 \times 10^{-3}$ kN/m and ranges preferably from $6 \times 10^{-3}$ to $70 \times 10^{-3}$ kN/m.

According to the present invention, the thermoplastic film contacting the base layer made of a fibrous non-woven web has preferably a thickness at most equal to 10 $\mu$m (micrometers) and, preferably, ranges from 5 $\mu$m to 8 $\mu$m.

According to a preferred embodiment, the thermoplastic film comprises at least one ethylene polymer associated with at least one anti-blocking agent.

The ethylene polymer may be selected from the group comprising copolymers of ethylene with at least one α-olefin having 3 to 8 carbon atoms, copolymers of ethylene/alkyl (meth)acrylate in which the alkyl group may be a linear or branched group having 1 to 6 carbon atoms, copolymers of ethylene and at least one vinyl ester of a saturated carboxylic acid having 2 to 6 carbon atoms.

By way of example, among the ethylene polymers are included low density polyethylene, very low density polyethylene, copolymers of ethylene/methyl(meth) acrylate, copolymers of ethylene/ethyl(meth)acrylate, copolymers of ethylene/butyl(meth)acrylate, copolymers of ethylene/vinyl acetate and mixtures of two or more of the foregoing.

Among these ethylene polymers, the invention concerns preferably the copolymers of ethylene/alkyl(meth)acrylate and more particularly the copolymers of ethylene/methylmethacrylate.

According to the present invention, preferably the copolymers of ethylene/alkyl(meth)acrylate comprise 2.5% to 40% by weight, preferably 15% to 30%, of units derived from alkyl(meth)acrylate.

They have a flow index in g/10 mn according to ISO 1133 standard (190° C.; load 2.16 kg) at least equal to 0.5 and preferably ranging from 3 to 10, and a specific gravity in g/cm$^3$ according to ISO 1183 standard ranging from 0.91 to 0.96.

The anti-blocking agent may be selected in the group comprising mineral fillers, amides of insaturated fatty acids having at least 8 carbon atoms, ethylene-bis-amides of insaturated fatty acids having at least 8 carbon atoms.

By way of example, among such anti-blocking agents are included silica, talc, zinc stearate, stearic amide, oleic amide, palmitic amide, erucic amide, myristic amide, behenic amide, ethylene-bis-oleamide, ethylene-bis-erucamide, ethylene-bis-stearamide.

In one embodiment talc and/or ethylene-bis stearamide are preferred.

These anti-blocking agents according to the present invention are used in amounts ranging from 0.01% to 2% by weight, and preferably 0.1 to 1.5% of anti-blocking agent based on the ethylene polymer.

According to the invention, the fibrous non-woven web may be manufactured by spun bonding and thermal bonding of substantially continuous filaments with molecular orientation, and having a weight per unit area ranging from 14 g/m$^2$ to 30 g/m$^2$; preferably the filaments have a diameter ranging from 1.8 to 2.2 dtex; furthermore, the addition of an additive such as (N-alkyl) amide of a fatty acid in an amount of 0.8 to 1% by weight based on the thermoplastic material improves the softness and the textile characteristics of the non-woven web.

Depending upon the shape of the patterns of the thermal bonding and the percentage of bonding points of the non-woven web, there is obtained a material having higher or lower elasticity and softness.

The non-woven webs obtained by any other manufacturing process such as spun lacing or intermingling with water jets, chemical bonding, thermal bonding, needling, melt-blowing, air-laid treatment or composite webs associating several different layers obtained by at least two of the said afore-mentioned processes may also be used.

Other type of synthetic fibers, for example polyethylene, polyester base fibers as well as mixtures thereof, having the same or different denier may be used.

"Spun" non-woven web containing a copolymer of ethylene/alkyl acrylate having a low melting point surface, which enhances adhesion, may also be used.

Another embodiment of the present invention concerns the use of such a coated non-woven material in a disposable absorbent hygiene article such as a diaper or a training pant, as a liquid impervious backsheet, the base layer made of a fibrous web being placed towards the outside of the diaper.

In another preferred embodiment, in a disposable absorbent hygiene article such as a diaper, the coated non-woven material may be used as a topsheet provided with a central opening and elastic elements which cooperate to facilitate passage of urine and feces and their isolation from the user's skin; in this case the base layer made of the fibrous web is placed so as to form the external face contacting the user's skin.

Also, the coated non-woven material may be used to form longitudinal, elasticized, leakproof barriers or flaps bonded in registration with or along the edges of the absorbent pad to the topsheet for the diaper. These flaps contact the user's thigh and prevent transverse leakages in direction of the longitudinal edges of the diaper; the base layer made of a fibrous web is also placed so as to be the external face contacting the user's skin.

BRIEF DESCRIPTION OF THE DRAWING FIGURES

DETAILED DESCRIPTION OF THE PREFERRED EMBODIMENTS

Figure 1:
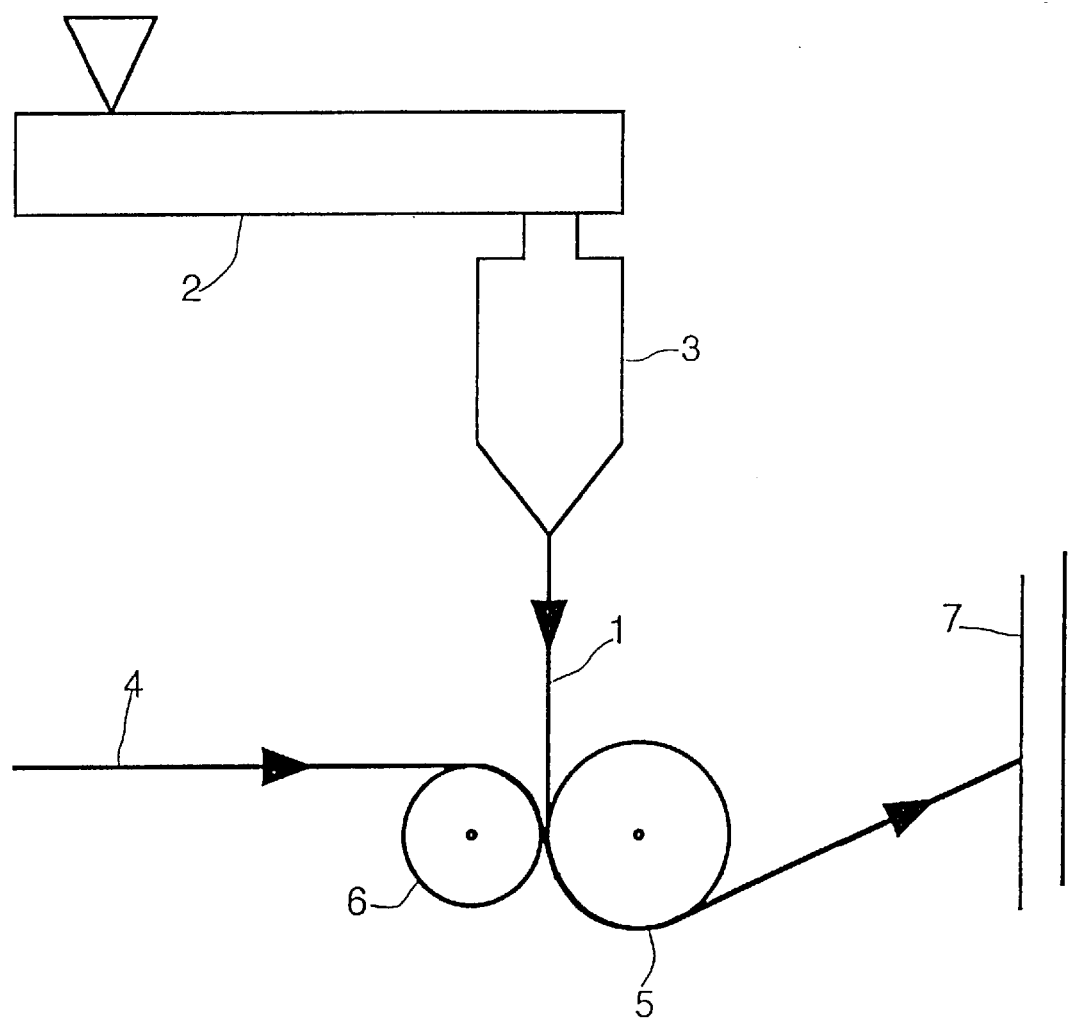
FIG. 1 is a schematic illustration of a process for making a coated non-woven material of the present invention.

The coated non-woven material according to the present invention may be obtained using the process schematically shown in FIG. 1 and which comprises:

In a first step, known in itself, extruding a thermoplastic film (1) with at least one extruder (2) having a die with adjustable gap.

This extruder is fed with a mixture comprising at least one ethylene polymer and at least one anti-blocking agent, said mixture optionally containing usual additives such as pigments, dyes and stabilizers.

Temperature of the material exiting the die may range from 280° C. to 320° C.

In a second step, the extruded thermoplastic film (1) having a temperature at most equal to 320° C., and not yet solidified, is contacted (applied) with a non-woven web (4). This film coating step is performed using two cylinders (5) and (6) between which the non-woven web (4) and the thermoplastic film (1) are fed. Cylinder (5) in direct contact with the thermoplastic film, which is generally designated as a "chill-roll", may be cooled by water at a temperature at most equal to 25° C., and, preferably, ranging from 15° C. to 20° C. Its surface may be glossy, mat or eventually grained.

According to the present invention the anti-blocking agent very highly reduces adhesion of the thermoplastic film to the chill-roll.

It is within the scope of the present invention to coat the chill-roll surface with an anti-adhesive coating such as Teflon® coating.

Pressure cylinder (6) which generally has a smaller diameter may also be cooled.

The pressure between the two cylinders may be at most equal to $6 \times 10^{-5}$ Pa and, preferably, ranges from 2 to $5 \times 10^{-5}$ Pa.

According to a preferred embodiment of the present invention, the distance between the die exit and the contact point between the plastic film and the non-woven web (distance generally designated as "air gap") is at most equal to 200 mm and, preferably, ranges from 50 to 150 mm.

In a third step, the non-woven web coated with the thermoplastic film is drawn using a drawing bench (7), the speed of which does not exceed 300 m/mn and, preferably, ranges from 100 to 150 m/mn. The drawing strength is low and perfectly controlled to prevent and deformation of the non-woven webs coated with the thermoplastic film. This strength does not exceed $5 \times 10^5$ Pa and ranges, preferably, from 2 to $3 \times 10^5$ Pa. Then, after having been submitted to an optional in line impression step on the external face of the film, the material is wound under a low tension strength.

By adjusting the extrusion temperature, flow rate, die gap, "air gap", pressure between the cylinders and their temperatures, drawing speed and strength, a non-woven material coated with a thermoplastic having a low thickness is obtained; nevertheless this low thickeness does not impair the imperviousness to liquid of the resulting material.

The film adheres uniformly only to the surface of the non-woven web.

The peel strength is low, being equal to or less than $98 \times 10^{-3}$ kN/m; it is, however, sufficient to provide processability for the intended uses. This fixing mode provides a material of high flexibility and which is not noisy upon rumpling. It has the advantage of retaining the initial tactile impression of the non-woven, in particular the fabric-like tactile impression.

The following example illustrates the invention.

The extruder used is a single screw extruder having a diameter D equal to 60 mm and a length of 30 D.

The extruder is fed with a mixture consisting of:

100 parts by weight of a mixture comprising 98.3% by weight of an ethylene/methyl acrylate copolymer including 20% by weight of units derived from methyl acrylate and 80% by weight of units derived from ethylene, having a flow index of 8 g/10 mn according to ISO 1133 standard (190 °C.; load 2.16 kg), 0.2% by weight of ethylene-bis-stearamide and 0.5% by weight of talc, commercialized by Company ELF ATOCHEM S.A. under the tradename LOTRYL 20 MB 08, and 7 parts by weight of a master batch of polyethylene containing 60% by weight of $TiO_2$.

Extrusion is performed at a temperature between 240° C. and 280° C. with a screw speed of 50 tr/mn and a flow rate of 50 kg/h. The die has a useful length of 900 mm and a gap width of 400 micrometers.

The film exiting the die is at 280° C. and is applied towards the two cylinders (5) and (6) to be deposited on a polypropylene non-woven web having a weight per unit area of 16 g/m² commercialized by the Company COROVIN GmbH under the tradename "CORONOVO DOUCE", the surface of the thermobonded areas of the non-woven web has a rated value of 6.88% and is comprised of 16 bonding points per square centimeter.

"Air gap" is 150 mm.

"Chill-roll" (5) is cooled with water at 18° C.

Pressure applied by pressure cylinder (6) is $2.10^{-5}$ Pa.

Line speed is 100 m/mn.

Drawing strength is about $3.10^5$ Pa.

The obtained non-woven material coated with a thermoplastic film is cut and wound.

Peel strength is measured on a coupon of the thus obtained material according to NFT 76-112 (May 1982) under the conditions; feeling aryle equal to 180°, full speed 200 mm/mn.

The peel strength is $15 \times 10^{-3}$ kN/m for a weight per unit area of 9.5 g/m² of the film; another example of coating a non-woven web of 20 g/m² with a film of 13 g/m² resulted in a peel strength of $70 \times 10^{-3}$ kN/m.

Observation with a scanning electronic microscope as well as a stereomicroscope using grazing incident light, of material components after delamination shows that adhesion occurs uniformly on the non-woven web material.

Figure 2:
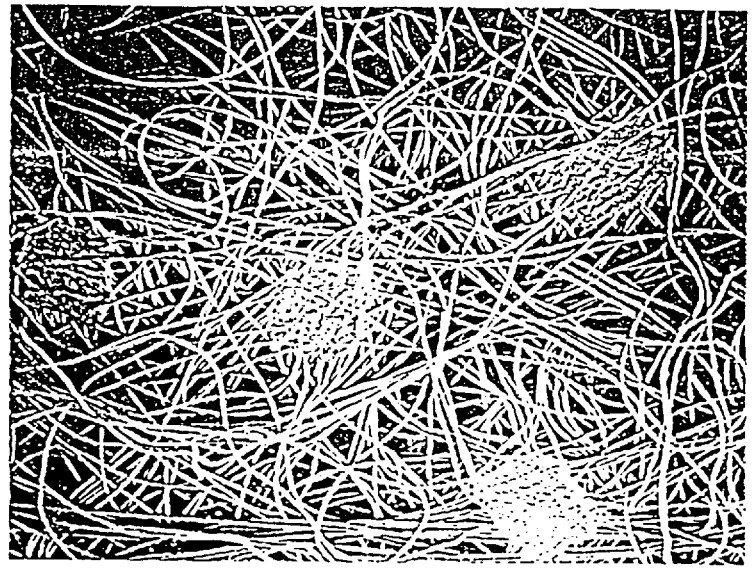
FIG. 2 is a magnified photographic image of a non-woven web surface according to the present invention, after delamination.

In FIG. 2, which is a photograph with a ×17 magnification of the non-woven web surface after delamination, i.e. after film separation, no trace of the thermoplastic film is observed. Intermingling of the continuous free fibers of the non-woven web has not been modified by separation of the thermoplastic film which indicates a partial superficial adhesion between the thermoplastic film and the non-woven web.

The areas where the non-woven web fibers appear partially melted, correspond in fact to bonding areas of the non-woven web (predensified areas).

Figure 3:
FIG. 3 is a magnified photographic image of a thermoplastic film according to the present invention, after delamination.

On the contrary in FIG. 3, which is a photograph obtained by stereomicroscopy with grazing light, and a magnification of ×12 of the surface of the thermoplastic film after delamination of the non-woven base layer, the impression of the surface fibres of the non-woven material which participated to the bonding is clearly visible.

This shows clearly that the thermoplastic film forms a coating of the surface fibres without substantial penetration into the non-woven material thickness.

Of course, the coated material of the invention may be used in numerous other application fields such as in the medical field, in particular for operative field, protective coatings, dressings and gloves.

What is claimed is:

1. A coated non-woven material having improved flexibility and fabric-like tactile impression, comprising a base layer made of a fibrous non-woven web and at least one layer made of a thermoplastic film the thermoplastic film is applied on the base layer, and has a peel strength which is equal to or below $98 \times 10^{-3}$ kN/m as measured according to the NFT 76-112 standard wherein a peeling angle of 180° and a pull speed of 200 mm/mn are utilized.

2. The material according to claim 1, wherein the peel strength ranges between $6 \times 10^{-3}$ and $70 \times 10^{-3}$ kN/m.

3. The material according to claim 1, wherein the thermoplastic film has a thickness equal to or below 10 μm.

4. The material according to claim 3, wherein the thermoplastic film has a thickness in a range of 5 to 8 μm.

5. The material according to claim 1, wherein the thermoplastic film comprises at least one polymer of ethylene and at least one antiblocking agent.

6. The material according to claim 5, wherein the polymer of ethylene is selected from the group consisting of: copolymers of ethylene and of at least an α-olefin having 3 to 8 carbon atoms, copolymers of ethylene/alkyl (meth)acrylate in which the alkyl group is linear or branched and contains from 1 to 6 carbon atoms, and copolymers of ethylene and of at least one vinyl ester of a saturated carboxylic acid containing from 2 to 6 carbon atoms.

7. The material according to claim 6, wherein the polymer of ethylene comprises copolymers of ethylene/alkyl (meth) acrylate.

8. The material according to claim 6, wherein the polymer of ethylene comprises copolymers of ethylene/methyl (meth)acrylate.

9. The material according to claim 8, wherein the polymer of ethylene comprises ethylene/methyl acrylate copolymer.

10. The material according to claim 7, wherein the ethylene/alkyl (meth)acrylate copolymers comprise 2.5% to 40% by weight of units derived from alkyl(meth)acrylate.

11. The material according to claim 5, wherein the antiblocking agent is selected from the group consisting of: mineral fillers, unsaturated fatty acid amides having at least 8 carbon atoms, and unsaturated fatty acid ethylene-bis-amides having at least 8 carbon atoms.

12. The material according to claim 11, wherein the anti-blocking agent is selected from the group consisting of: silica, talc, zinc stearate, stearic, oleic, palmitic, erucic, myristic, behenic amides, ethylene-bis-oleamide, ethylene-bis-erucamide, and ethylene-bis-stearamide.

13. The material according to claim 11, wherein the anti-blocking agent is chosen from the group consisting of: talc, ethylene-bis-stearamide, and a combination of talc and ethylene-bis-stearamide.

14. The material according to claim 1, wherein the fibrous non-woven web is a spun bonded fabric made from essentially continuous, molecularly oriented filaments of polypropylene, and has a weight per unit area ranging between 14 g/m² and 30 g/m².

15. The material according to claim 14, wherein the polypropylene based composition is modified by adding 0.8 to 1% by weight of a fatty acid (N-alkyl) amide and that the filaments have a diameter ranging from 1.8 to 2.2 dtex.

16. A method of manufacturing a coated non-woven material according to claim 1 comprising:

extruding a thermoplastic film, heat bonding the film to a non-woven web at a temperature not above 320° C. by using two cylinders pressed together with a pressure not above $6 \times 10^5$ Pa, and drawing the coated non-woven web using a drawing bench at a speed below 300 m/mn with a drawing tension below $5 \times 10^5$ Pa.

17. A disposable absorbent hygiene article comprising a liquid impervious backsheet made of the material according to claim 1, with a base layer of the backsheet made of the fibrous web oriented to face outwardly.

18. A disposable absorbent hygiene article in which a coversheet is provided, the coversheet having a central aperture and elastic elements cooperating with the central aperture, the coversheet is made of the material according to claim 1, with a base layer of the coversheet made of a fibrous web oriented to be an external face in contact with a user's skin.

19. A disposable absorbent hygiene article comprising flaps or longitudinal elasticized leakage barriers fixed above an absorbent pad, or along longitudinal edges of the pad, to an internal coversheet of the article, the flaps are made of the material according to claim 1, with a base layer made of the fibrous web oriented to be an external face in contact with a user's skin.

20. The article of claim 17, wherein said disposable hygiene article comprises one of a diaper and a training pant.

21. The article of claim 18, wherein said disposable hygiene article comprises a diaper.

22. The article of claim 19, wherein said disposable hygiene article comprises a diaper.

* * * * *